(12) United States Patent
Chang et al.

(10) Patent No.: US 12,089,961 B2
(45) Date of Patent: Sep. 17, 2024

(54) SIGNAL QUALITY DETECTION METHOD AND SIGNAL DETECTION DEVICE THEREOF

(71) Applicant: Wistron Corporation, New Taipei (TW)

(72) Inventors: Hsuan-Tsung Chang, New Taipei (TW); Kuo-Ting Huang, New Taipei (TW); Ching-An Cho, New Taipei (TW); Hao-Gong Chou, New Taipei (TW)

(73) Assignee: Wistron Corporation, New Taipei (TW)

( * ) Notice: Subject to any disclaimer, the term of this patent is extended or adjusted under 35 U.S.C. 154(b) by 923 days.

(21) Appl. No.: 17/145,375

(22) Filed: Jan. 10, 2021

(65) Prior Publication Data
US 2022/0160308 A1 May 26, 2022

(30) Foreign Application Priority Data

Nov. 25, 2020 (TW) .................................. 109141292

(51) Int. Cl.
*A61B 5/00* (2006.01)
(52) U.S. Cl.
CPC .......... *A61B 5/7221* (2013.01); *A61B 5/6815* (2013.01); *A61B 5/7225* (2013.01); *A61B 5/7246* (2013.01)
(58) Field of Classification Search
CPC ... A61B 5/7246; A61B 5/7225; A61B 5/6815; A61B 5/7221
See application file for complete search history.

(56) References Cited

U.S. PATENT DOCUMENTS

| 2004/0138540 A1* | 7/2004 | Baker, Jr. ............... | A61B 5/145 600/336 |
| 2006/0094943 A1* | 5/2006 | Van Slyke ......... | A61B 5/14551 600/323 |
| 2010/0249551 A1* | 9/2010 | Miller ................ | A61B 5/14551 600/323 |

FOREIGN PATENT DOCUMENTS

| CN | 103596491 A | * | 2/2014 | ......... A61B 5/02405 |
| TW | 201306795 A | * | 2/2013 | ............... F16J 15/46 |

(Continued)

OTHER PUBLICATIONS

Geoffrey Clarke, "Signal Quality Analysis in Pulse Oximetry: Modelling and Detection of Motion Artifact," May 2015, Carleton University (Year: 2015).*

(Continued)

*Primary Examiner* — Natalie Huls
*Assistant Examiner* — Nyla Gavia
(74) *Attorney, Agent, or Firm* — Winston Hsu

(57) ABSTRACT

The present invention provides a signal quality detection method for an ear-chip physiological measurement device. The signal quality detection method includes receiving a sensing signal from the ear-clip physiological measurement device; filtering the sensing signal to generate a pre-processed signal; calculating a physiological index according to the pre-processed signal; and calculating a similarity of a red light alternating current (AC) component and an infrared light AC component of the pre-processed signal and a plurality of correlation coefficients of the red light AC component, and generating a reliability index of the physiological index accordingly. The reliability index indicates one of a plurality of signal qualities.

18 Claims, 8 Drawing Sheets

(56) References Cited

FOREIGN PATENT DOCUMENTS

TW    I432175 B      4/2014
TW    I720215 B  *   6/2017  ............... A61B 5/11

OTHER PUBLICATIONS

Clarke ,Signal Quality Analysis in Pulse Oximetry: Modelling and Detection of Motion Artifact ,May 2015.

* cited by examiner

SIGNAL QUALITY DETECTION METHOD AND SIGNAL DETECTION DEVICE THEREOF

BACKGROUND OF THE INVENTION

1. Field of the Invention

The present invention relates to a signal quality detection method and signal detection device thereof for an ear-chip physiological measurement device, and more particularly, to a signal quality detection method and signal detection device thereof capable of indicating a reliability index of a detected physiological index in real time, to assist a user to adjust the wearing position accordingly and have higher accuracy.

2. Description of the Prior Art

Photoplethysmography (PPG) may non-invasively detect the volume change of the blood, and thus measure physiological indexes such as heart rates, blood oxygen concentration. In short, sensing elements of Photoplethysmography mainly include light-emitting diodes and photodiodes. The light-emitting diodes emit light, and the photodiodes receive light signals passing through vessels. The alternating current (AC) component of the light signal reflects blood changes caused by the heart beats, and the direct-current (DC) component of the light signal reflects unchanged light absorption of the subcutaneous tissue, venous blood, etc. The light signals measured by Photoplethysmography are easily interfered by external noise. The low-frequency noise is mostly caused by motion and breathing, which will cause amplitude drift in the DC component. The high-frequency noise is mostly caused by the ambient light, which will cause disturbances in the AC component.

Most current wearable devices for measuring blood oxygen concentration are finger-clip blood oxygen pulse machines, which usually cover the object to be measured to isolate external light. Normal oxygen measuring devices may change the probe to function as clip-type or patch-type. Current references compare measurement positions such as fingers, earlobes, foreheads and toes and conclude that there is relatively high accuracy for an earlobe probe. However, the conventional ear-clip device faces two major challenges when measuring blood oxygen concentration. First of all, it is not possible to visually tell whether the wearing position is bad. The user's ear is prone to not closely attach the device sensor such that the emitted light scatters or the photodiode receives the noise including external light source. Secondly, the sensor uses a reflective light module, which cannot completely isolate external noise. In this case, if the signal quality of the red light waveform for measuring blood oxygen concentration is not good, it will greatly affect the accuracy of calculation of blood oxygen concentration. In addition, physiological data will also fluctuate in values due to various factors, which causes inaccuracy in the user's record.

Therefore, it is necessary to improve the prior art.

SUMMARY OF THE INVENTION

It is therefore an objective of the present invention to provide a signal quality detection method and signal detection device thereof capable of indicating a reliability index of a detected physiological index in real time, to assist a user to adjust the wearing position accordingly and have higher accuracy.

The present invention discloses a signal quality detection method for an ear-chip physiological measurement device. The signal quality detection method includes receiving a sensing signal from the ear-clip physiological measurement device; filtering the sensing signal to generate a pre-processed signal; calculating a physiological index according to the pre-processed signal; and calculating a similarity of a red light alternating current (AC) component and an infrared light AC component of the pre-processed signal and a plurality of correlation coefficients of the red light AC component, and generating a reliability index of the physiological index accordingly. The reliability index indicates one of a plurality of signal qualities.

The present invention further discloses a signal detection device for an ear-chip physiological measurement device. The signal detection device includes an input module, for receiving a sensing signal from the ear-clip physiological measurement device; a pre-processed module, for filtering the sensing signal to generate a pre-processed signal; a processor, for executing a program code; and a storage unit, coupled to the processor, for storing the program code. The program code is utilized for instructing the processor to perform following steps: calculating a physiological index according to the pre-processed signal; and calculating a similarity of a red light alternating current (AC) component and an infrared light AC component of the pre-processed signal and a plurality of correlation coefficients of the red light AC component, and generating a reliability index of the physiological index accordingly. The reliability index indicates one of a plurality of signal qualities.

These and other objectives of the present invention will no doubt become obvious to those of ordinary skill in the art after reading the following detailed description of the preferred light embodiment that is illustrated in the various figures and drawings.

DETAILED DESCRIPTION

In general, for blood oxygen concentration measurement, the Photoplethysmography (PPG) utilizes lights with two different wavelength spectrums, such as red light and infrared light, to determine absorption variation of different components in body tissues. Specifically, the heart is systolic and diastolic to cause pulsations and vascular volume change, and heme with oxygen and heme without oxygen in the blood will change accordingly, which also affect the degree of light absorption. Therefore, intensities of lights received by the light sensors are different, and a tiny alternating current (AC) signal is generated. Blood oxygen signals received by the oximeter in red lights and infrared lights may be divided into direct-current (DC) components $DC_{Red}$, $DC_{IR}$ and AC components $AC_{Red}$, $AC_{IR}$, and a ratio R may be derived from an equation (1), and then blood oxygen concentration is obtained from the ratio R via experimental analysis:

$$R = \frac{AC_{Red}/DC_{Red}}{AC_{IR}/DC_{IR}} \qquad \text{eq. (1)}$$

Since the red light blood absorption rate is high, variance of reflected light intensities is small. In other words, the amplitude of the red light is small and thus noise is relatively large, the red light AC component $AC_{Red}$ is susceptible to interference and the waveform signal has low quality, causing errors in the calculation of blood oxygen concentration.

Figure 1:
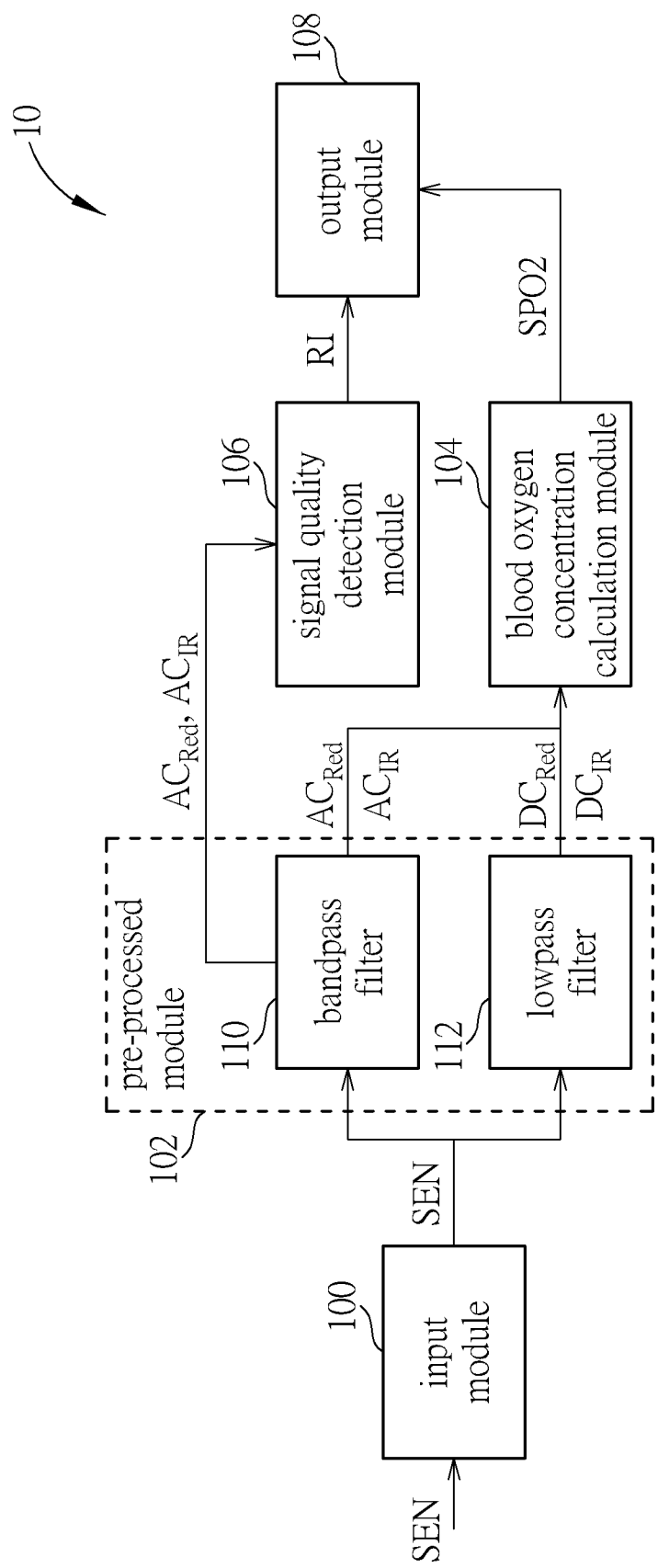
FIG. 1 is a schematic diagram of a signal detection device according to an embodiment of the present invention.

Please refer to a FIG. 1, which is a schematic diagram of a signal detection device 10 according to an embodiment of the present invention. The signal detection device 10 is utilized for an ear-clip physiological measurement device (such as a Thor ear-clip device), the ear-clip physiological measurement device is in contact with the wall of the ear, and includes a Photoplethysmography module for transmitting and receiving green lights, red lights and infrared lights, to generate a sensing signal SEN. In short, the signal detection device 10 includes an input module 100, a pre-processed module 102, a blood oxygen concentration calculation module 104, a signal quality detection module 106, and an output module 108. The input module 100 may receive the sensing signal SEN from the ear-clip physiological measurement device (such as including a transmission module for transmission via wireless transmission such as Bluetooth or WiFi, or transmission via a transmission line). The pre-processed module 102 may filter the sensing signal SEN to generate the pre-processed signal. For example, the pre-processed module 102 may include a bandpass filter 110 and a lowpass filter 112. The bandpass filter 110 performs bandpass filtering on the sensing signal SEN to generate a red light AC component $AC_{red}$ and an infrared light AC component $AC_{IR}$ of the pre-processed signal, and the lowpass filter 112 performs lowpass filtering on the sensing signal SEN to generate a red light DC component $DC_{Red}$ and an infrared light DC component $DC_{IR}$ of the pre-processed signal. The blood oxygen concentration calculation module 104 calculates a physiological index according to the pre-processed signal, e.g. the blood oxygen concentration calculation module 104 calculates an oxygen concentration SPO2 (or other physiological indexes such as heart rate, etc.) according to the red light AC component $AC_{red}$, the infrared light AC component $AC_{IR}$, the red light DC component $DC_{Red}$ and the infrared light DC component $DC_{IR}$ of the pre-processed signal. The signal quality detection module 106 calculates a similarity of the red light AC component $AC_{red}$ and the infrared light AC component $AC_{IR}$ and a plurality of correlation coefficients of the red light AC component $AC_{red}$, and generates a reliability index RI of the physiological index (e.g. the oxygen concentration SPO2) accordingly. The reliability index RI indicates one of a plurality of signal qualities. The output module 108 outputs the physiological index (e.g. the oxygen concentration SPO2) and the reliability index RI (e.g., via a screen for image output, via a blinking light, or via a speaker for sound output, etc.).

Under such a situation, the ear-clip physiological measurement device may be set to transmit the sensing signal SEN every 2 seconds, so that the signal detection device 10 may update and output the blood oxygen concentration SPO2 and the reliability index RI every 2 seconds to achieve real-time measurement. Furthermore, for the lowest 40 beats per minute (BPM), every heartbeat at least requires 1.5 seconds and a 2-second sample window ensures that at least one complete cycle of the pulse wave is sampled, which avoiding sampling different parts of a cycle and resulting differences. Subsequently, the components of the pre-processed (filtered) signal are calculated for the blood oxygen concentration SPO2 and the and reliability index RI of a corresponding segment of the sensing signal SEN. Thus, the user may adjust the wearing position according to whether a signal quality indicated by the reliability index RI is a high signal quality, a medium signal quality or a low signal quality, and interpret the blood oxygen concentration SPO2 according to the reliability index RI. As a result, the present invention may indicate the reliability index RI of the detected physiological index in real time, to assist the user to adjust the wearing position accordingly and thus have high accuracy.

Specifically, after the pre-processed module 102 samples and eliminates ambient lights for the sensing signal SEN, the bandpass filter 110 and the low pass filter 112 (such as Butterworth filter for smoothing a frequency response curve in a frequency band) may extract the red light AC component $AC_{red}$, the infrared light AC component $AC_{IR}$, the red light DC component $DC_{Red}$ and the infrared light DC component $DC_{IR}$. It is worth noting that the cut-off frequency of the band-pass filter 110 may be designed to be 0.5-5 Hertz (Hz). Take extreme heart rate values of 40 and 250 as an example, the heart rates of 0.667 Hz and 4.167 Hz respectively fall within the bandpass range. Compared with a high-pass filter, the bandpass filter 110 filters out the noise of the ambient lights, so that the waveform is smoother, so that a more accurate blood oxygen concentration may be calculated.

Next, the blood oxygen concentration calculation module 104 may utilize different wavelength spectrums of the red light and infrared, to estimate a saturation ratio of heme with oxygen and heme without oxygen in the blood vessel, i.e. obtains the ratio R according to the red light AC component $AC_{red}$, the infrared light AC component $AC_{IR}$, the red light DC component $DC_{Red}$ and the infrared light DC component $DC_{IR}$ and according to equation (1), and obtains the blood oxygen concentration via experimental analysis. In this case, the ratio value R is generally calculated by the peak and valley detection method to calculate a perfusion index (PI), i.e. a ratio of the AC component to the DC component, with detected extreme values. A clean signal may be successfully detected every two extreme values of each pulse wave, while a waveform with noise interference is easily false determined or missed right extreme values. Thus, another calculation is to perform a root mean square (RMS) method and then derive the perfusion index with the ratio of the AC component to the DC component. Compared with only calculating peaks and valleys, this method will take every point in the signal to calculate an amplitude of the root mean square. The present invention calculates the AC component and the DC component every 2 seconds to reduce the influence brought by the mean amplitude. Calculations of the blood perfusion index using the peak and valley detection method or the root mean square method are well known to those skilled in the art, and will not be narrated here for the sake of brevity. As a result, the embodiment of the present invention may adopt the root mean square calculation method to calculate the ratio R, to avoid motion artifacts and noise, but other embodiments may adopt the peak and valley detection method, and are not limited thereto.

On the other hand, clinical testing should prevent the interference of external noise or the light leakage caused by poor wearing from affecting the signal quality, but it is usually difficult for users to determine whether the measurement is good or bad while bad waveforms will cause measured light values incorrect. The signal quality detection module 106 may generate the reliability index RI to divide the signal quality of the sensing signal SEN into low, medium, and high, to help users easily decide whether the current sensing signal SEN is good. If the signal quality is low, the reliability of the measured blood oxygen concentration SPO2 is low, and the user must re-adjust the wearing position of the device. If the signal quality is medium, the measured blood oxygen concentration SPO2 is trustworthy, and the user may or may not fine-tune the wearing position of the device. If the signal quality is high, the oxygen concentration SPO2 is accuracy data with high reliability, and the user does not need to change the wearing position of the device. In other embodiments, the reliability index RI may indicate one of other number of signal qualities, so that the user may adjust the wearing position of the device accordingly.

Specifically, the signal quality detection module 106 adopts two signal quality indexes (SQI), and utilizes combinations of different weights to achieve automatic classification of signal qualities of waveforms. The two signal quality indexes are a plurality of correlation coefficients $SQI_{xcorr}$ of the red light AC component $AC_{Red}$ and a similarity $SQI_{RICORR}$ of the red light AC component $AC_{Red}$ and the infrared light AC component $AC_{IR}$. The plurality of correlation coefficients $SQI_{xcorr}$ of the red light are utilized for determining whether the signal is stable and is not interfered by noise, while the similarity $SQI_{RICORR}$ of the red light and infrared light is utilized for determining light leakage (i.e. emitters of the red light and the infrared light are at different positions of the ear-clip physiological measurement device, and if peaks and valleys of the received red light and the received infrared light are not matched and are not similar, it means that the ear-clip physiological measurement device is not closely attached, causing light leakage).

Figure 2:
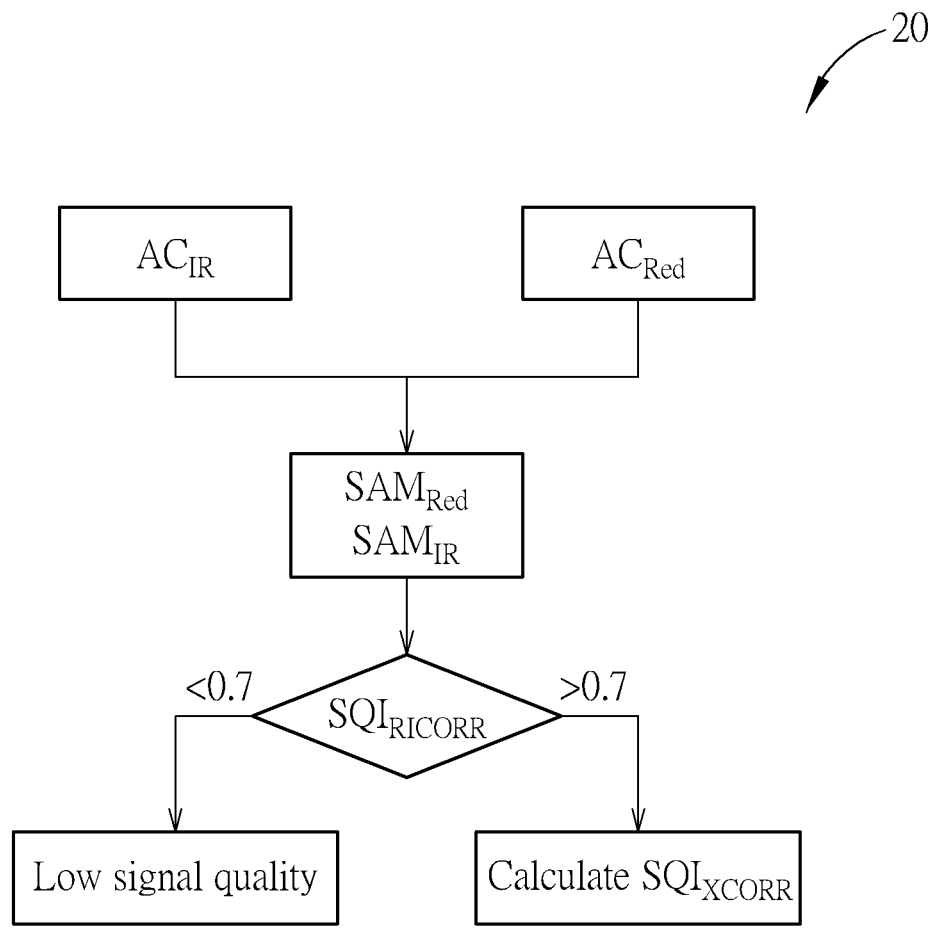
FIG. 2 is a schematic diagram of a similarity determination process according to an embodiment of the present invention.

Please refer to FIG. 2, which is a schematic diagram of a similarity determination process 20 according to an embodiment of the present invention. As shown in FIG. 2, the signal quality detection module 106 retrieves the red light AC component $AC_{Red}$ and the infrared light AC component $AC_{IR}$ within a sample period as a red light sample signal $SAM_{Red}$ and an infrared light sample signal $SAM_{IR}$ (e.g. if the sample period is 2 seconds, periods of the red light sample signal $SAM_{Red}$ and the infrared light sample signal $SAM_{IR}$ are also 2 seconds, respectively). Then, the signal quality detection module 106 calculates the similarity $SQI_{RICORR}$ of the red light sample signal $SAM_{Red}$ and the infrared light sample signal $SAM_{IR}$. When the similarity $SQI_{RICORR}$ is less than a similarity threshold (e.g. 0.7), the reliability index RI indicates the signal with a low signal quality. When the similarity $SQI_{RICORR}$ is greater than the similarity threshold (e.g. 0.7), the signal quality detection module 106 continues to calculate the plurality of correlation coefficients $SQI_{xcorr}$ of the red light AC component $AC_{Red}$. The similarity $SQI_{RICORR}$ (such as a correlation coefficient) is calculated as shown in equation (2) (wherein x and y, respectively, may be the red light sample signal $SAM_{Red}$ and the infrared light sample signal $SAM_{IR}$):

$$SQI_{RICORR} = \frac{\Sigma(x_i - \bar{x})(y_i - \bar{y})}{\sigma_x \sigma_y} \qquad \text{eq. (2)}$$

Figure 3:
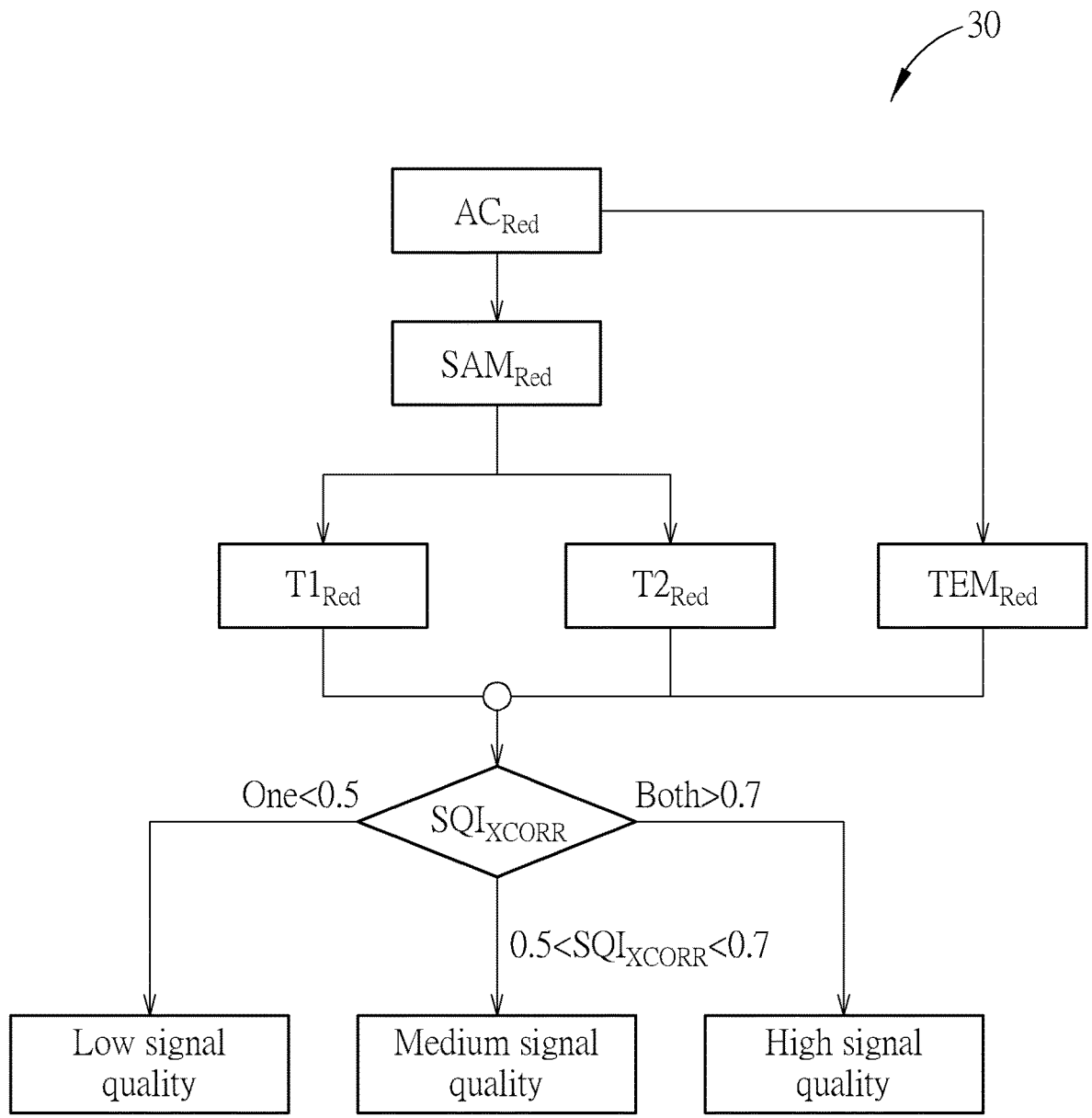
FIG. 3 is a schematic diagram of a red light correlation determination process according to an embodiment of the present invention.

Please refer to FIG. 3, which is a schematic diagram of a red light correlation determination process 30 according to an embodiment of the present invention. When the similarity $SQI_{RICORR}$ is greater than the similarity threshold as shown in FIG. 2, the red light correlation determination process 30 is performed. As shown in FIG. 3, the signal quality detection module 106 utilizes the red light AC component $AC_{Red}$ retrieved within a previous sample period as a template signal $TEM_{Red}$ (i.e., the previous red light sample signal), and divides the red light sample signal $SAM_{Red}$ retrieved within a current sample period into red light test signals $T1_{Red}$, $T2_{Red}$ (e.g. dividing the red light sample signal $SAM_{Red}$ from a midpoint into two red light test signals $T1_{Red}$, $T2_{Red}$ with respective periods of 1 sec, or red light test signals with other number or other respective periods in other embodiments). The signal quality detection module 106 calculates two correlation coefficients $SQI_{xcorr}$ of the red light test signals $T1_{Red}$, $T2_{Red}$ and the template signal $TEM_{Red}$. Next, the signal quality detection module 106 generates the reliability index RI indicating one of the high, medium and low signal qualities according to the two correlation coefficients $SQI_{xcorr}$ and a plurality of correlation thresholds. For example, if one the two correlation coefficients $SQI_{xcorr}$ is less than a first correlation threshold (e.g. 0.5), the signal quality detection module 106 generates the reliability index RI indicating a low signal quality. If the two correlation coefficients $SQI_{xcorr}$ are between the first correlation threshold and a second threshold correlation (e.g. 0.5 to 0.7), the signal quality detection module 106 generates the reliability index RI indicating a medium signal quality. If the two correlation coefficients $SQI_{xcorr}$ are greater than the second correlation threshold (e.g. 0.7), the signal quality detection module 106 generates the reliability index RI indicating a high signal quality.

Figure 4:
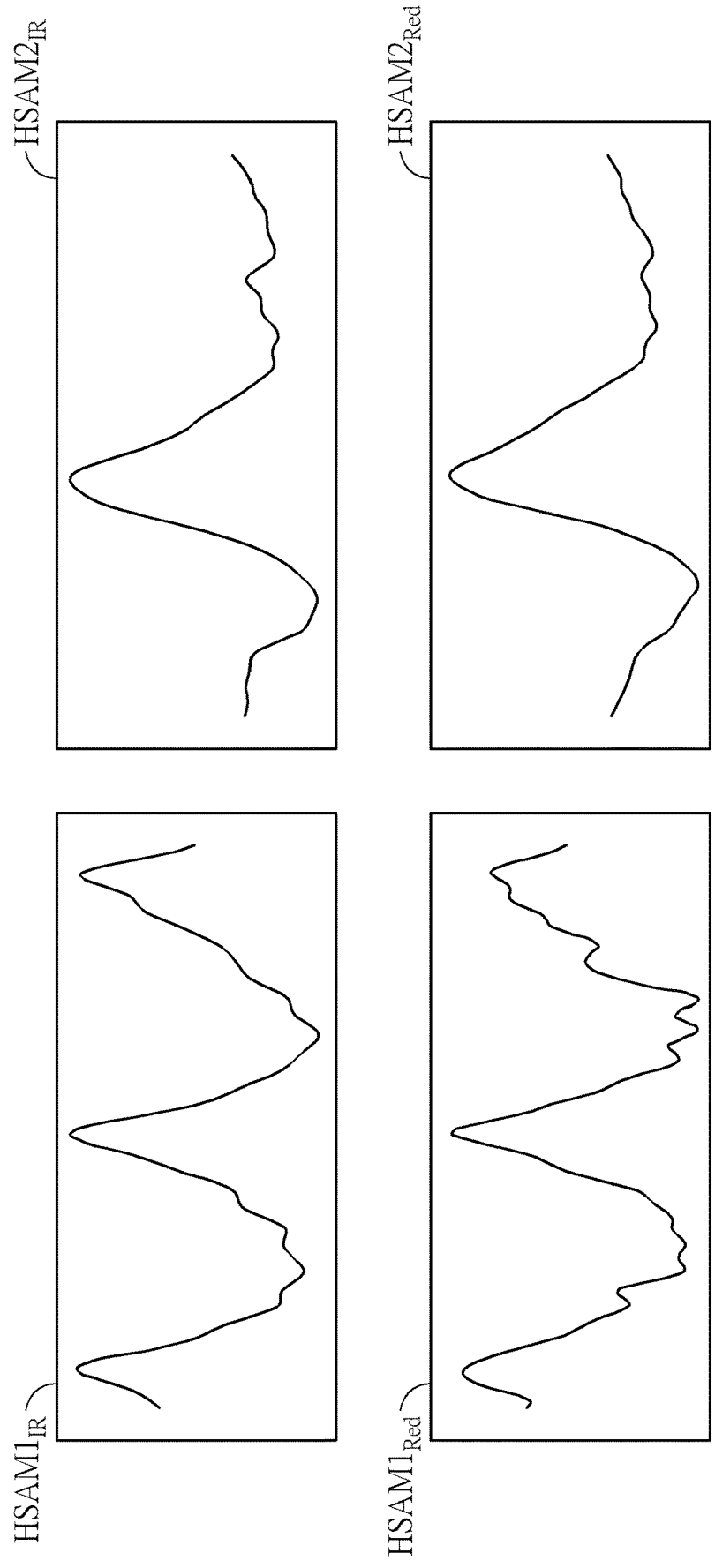
FIG. 4 is a schematic diagram of waveforms indicated by the reliability index as high signal qualities according to an embodiment of the present invention.

For example, please refer to FIG. 4, which is a schematic diagram of waveforms indicated by the reliability index RI as high signal qualities according to an embodiment of the present invention. As shown in FIG. 4, the left side of FIG. 4 illustrates an infrared light sample signal $HSAM1_{IR}$ and a red light sample signal $HSAM1_{Red}$ of a test subject in an upper part and a lower part, respectively. Peaks and valleys of the infrared light sample signal $HSAM1_{IR}$ and the red light sample signal $HSAM1_{Red}$ are substantially aligned, which indicates high similarity, and noise impact on the red light sample signal $HSAM1_{Red}$ is small and the waveform has regular periodicity, which indicates high correlation coefficients (the template signal is also assumed to have the waveform with regular periodicity). Thus, the infrared light sample signal $HSAM1_{IR}$ and the red light sample signal $HSAM1_{Red}$ have a high signal quality. An infrared light sample signal $HSAM2_{IR}$ and a red light sample signal $HSAM2_{Red}$ of another test subject illustrated in an upper part and a lower part of the right side of FIG. 4, respectively, also have similar features and thus have a high signal quality.

Figure 5:
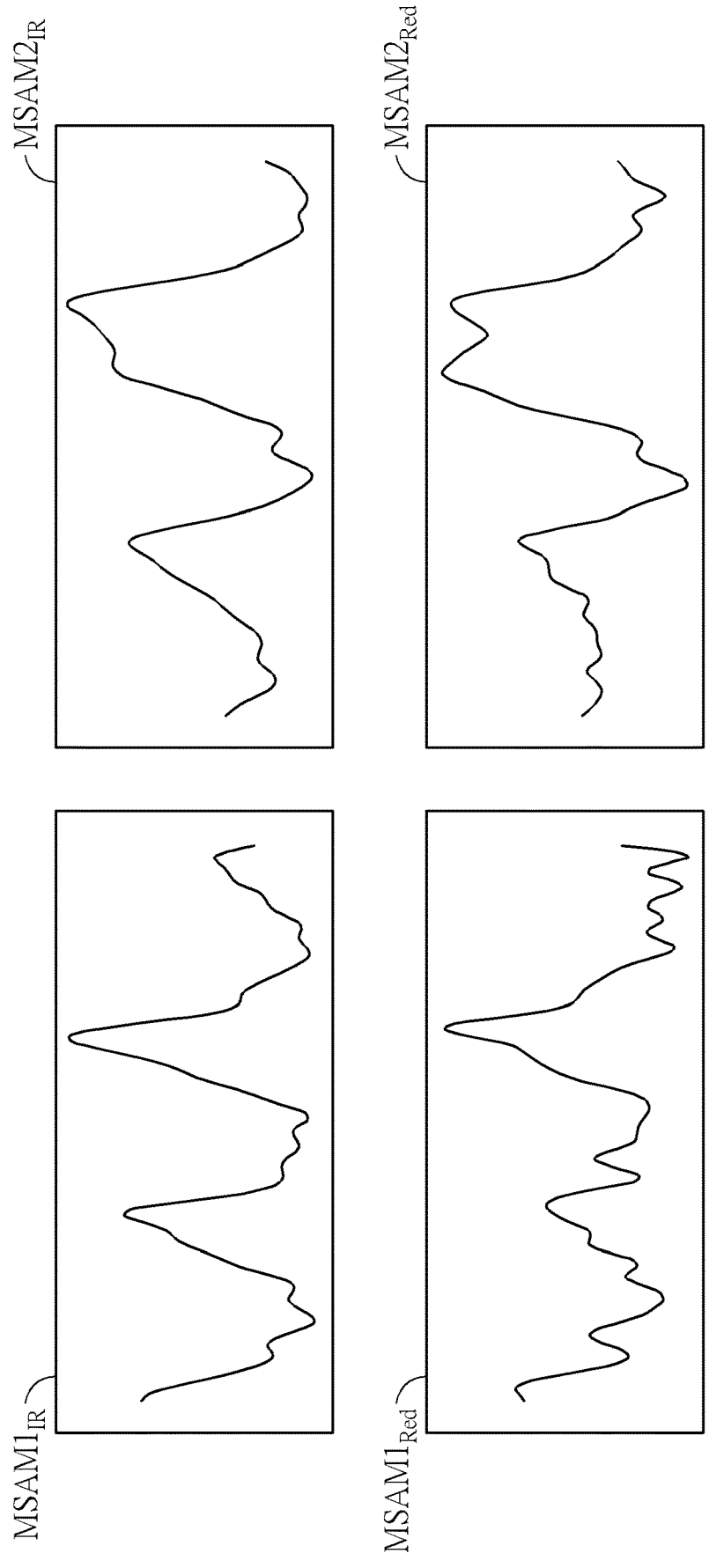
FIG. 5 is a schematic diagram of waveforms indicated by the reliability index as medium signal qualities according to an embodiment of the present invention.

On the other hand, please refer to FIG. 5, which is a schematic diagram of waveforms indicated by the reliability index RI as medium signal qualities according to an embodiment of the present invention. As shown in FIG. 5, the left side of FIG. 5 illustrates an infrared light sample signal $MSAM1_{IR}$ and a red light sample signal $MSAM1_{Red}$ of a test subject in an upper part and a lower part, respectively. Peaks and valleys of the infrared light sample signal $MSAM1_{IR}$ and the red light sample signal $MSAM1_{Red}$ are substantially aligned, which indicates high similarity, while the red light sample signal $MSAM1_{Red}$ is influenced by noise but still has regular periodicity, which indicates medium correlation coefficients (the template signal is also assumed to have the waveform with regular periodicity). Thus, the infrared light sample signal $MSAM1_{IR}$ and the red light sample signal $MSAM1_{Red}$ have a medium signal quality. An infrared light sample signal $MSAM2_{IR}$ and a red light sample signal $MSAM2_{Red}$ of another test subject illustrated in an upper part and a lower part of the right side of FIG. 5, respectively, also have similar features and thus have a medium signal quality.

Figure 6:
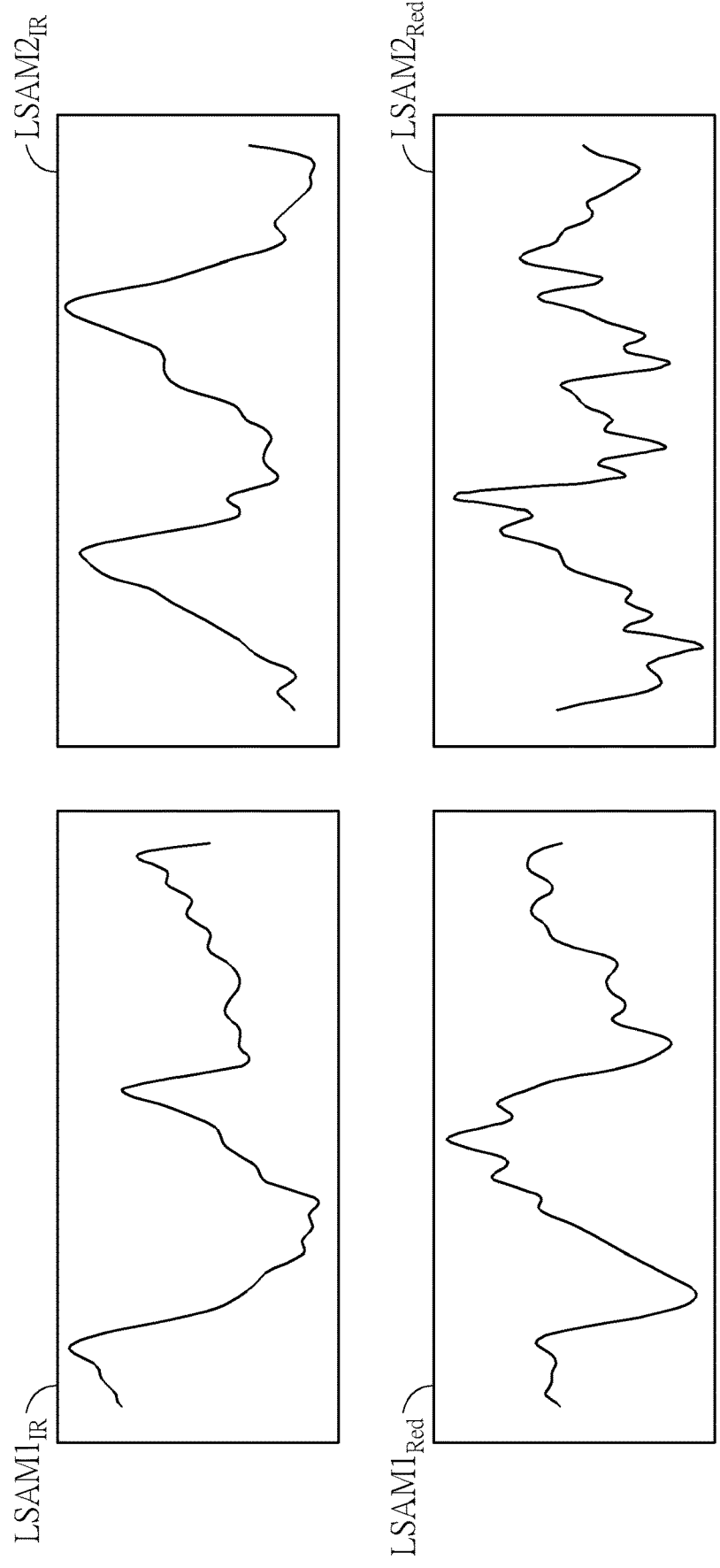
FIG. 6 is a schematic diagram of waveforms indicated by the reliability index as low signal qualities according to an embodiment of the present invention.

On the other hand, please refer to FIG. 6, which is a schematic diagram of waveforms indicated by the reliability index RI as low signal qualities according to an embodiment of the present invention. As shown in FIG. 6, the left side of FIG. 6 illustrates an infrared light sample signal $LSAM1_{IR}$ and a red light sample signal $LSAM1_{Red}$ of a test subject in an upper part and a lower part, respectively. Peaks and valleys of the infrared light sample signal $LSAM1_{IR}$ and the red light sample signal $LSAM1_{Red}$ are not aligned due to interference of noise or light leakage, which indicates low similarity. Thus, the infrared light sample signal $LSAM1_{IR}$ and the red light sample signal $LSAM1_{Red}$ have a low signal quality. The right side of FIG. 6 illustrates an infrared light sample signal $LSAM2_{IR}$ and a red light sample signal $LSAM2_{Red}$ of another test subject in an upper part and a lower part, respectively. Peaks and valleys of the infrared light sample signal $LSAM2_{IR}$ and the red light sample signal $LSAM2_{Red}$ are substantially aligned after shifting, which indicates enough similarity, while the red light sample signal $LSAM2_{Red}$ is influenced by noise and has no periodicity, which indicates low correlation coefficients (the template signal is also assumed to have the waveform with regular periodicity). Thus, the infrared light sample signal $LSAM2_{IR}$ and the red light sample signal $LSAM2_{Red}$ have a low signal quality.

In addition, calculation of the correlation coefficients $SQI_{xcorr}$ is detailed as follows. First, a correlation coefficient $\rho_{XY}[n]$ represents a correlation coefficient of a test signal X and a template signal Y in n time points (the test signal X may be one of the red light test signals $T1_{Red}$, $T2_{Red}$ and the template signal Y may be the template signal the $TEM_{Red}$) as shown in equation (3):

$$\max(\rho_{XY}[n]) = \max(\Sigma_{m=0}^{2f_s}(X_{NORM}[m])(Y_{NROM}[m+n])) \quad (3)$$

$X_{NORM}$ represents the test signal of a second after normalization, and $Y_{NROM}$ represents the template signal of 2 seconds after normalization. To calculate a ratio of correlation, it needs to compare with the maximum possible measured correlation. That is, the autocorrelation coefficient $\max(\rho\_YY[n])$ of the template signal of 2 seconds, and the maximum value occurs at time displacement 0. It shall scale half the ratio for the correlation coefficient of the test signal of 1 second, which may be simplified as equation (4):

$$\max(\rho_{YY}[n]/2) = (\Sigma_{m=0}^{2f_s}(Y_{NROM}[m])^2)/2 \quad \text{eq. (4)}$$

The correlation coefficient $SQI_{xcorr}$ may be defined as equation (5), which represents a correlation coefficient of the test signal and the template signal in comparison with the autocorrelation coefficient of the template signal. If the correlation coefficient $SQI_{xcorr}$ is close to 1, it represents that the test signal and the template signal are similar, and vice versa. Two test signals of 1 second are both required to have a certain degree of similarity, to indicate a high signal quality. If one of the test signals of 1 second has similarity lower than the similarity threshold, it indicates a low signal quality.

$$SQI_{XCORR} = \frac{2\max(\rho_{XY})}{\max(\rho_{YY})} \quad \text{eq. (5)}$$

Under such a situation, the plurality of correlation coefficients $SQI_{xcorr}$ of the red light AC component $AC_{Red}$ have features of periodicity of the pulse signal. The current red light sample signal $SAM_{Red}$ of 2 seconds are divided into the current red light test signal $T1_{Red}$, $T2_{Red}$ of 1 second, and the previous red light sample signal is utilized as the template signal $TEM_{Red}$. Advantages of calculating the correlation coefficients with the current red light test signal $T1_{Red}$, $T2_{Red}$ of 1 second and the template signal $TEM_{Red}$ are as follows:

1. Reduce false determination: the correlation coefficients $SQI_{xcorr}$ of the two sampled test signals $T1_{Red}$, $T2_{Red}$ are required to be above the correlation threshold, which reduces the possibility that signals with low signal quality are similar and determined as high signal quality (it is very unlikely that the two sample signals $T1_{Red}$, $T2_{Red}$ are both bad and similar to the sample signal $TEM_{Red}$)
2. Reduce influence of filtering distortion: the test signals $T1_{Red}$, $T2_{Red}$ are filtered first, and shorter signal is prone to have slight distortion at the edge after filtering (e.g. the entire waveform is not retrieved, and different sampled points result different influences, e.g. the edge with large slope variation affects the calculated result more), such that the 2 test signals $T1_{Red}$, $T2_{Red}$ are utilized, to avoid one test signal prone to distortion.
3. Avoid false determination due to surges: high amplitude caused by a surge results in a high correlation coefficient (the surge is a strong signal and a high correlation coefficient value is calculated when the surge is moved to match the peak of the template signal $TEM_{Red}$, such that a false high similarity is determined when remaining waveform is not similar), and 2 sampled test signals ensure to exclude surges (i.e. a surge is sporadic, and not consecutive, and thus 2 sampled test signals avoid false determination of high signal quality when a surge is in one sampled test signal).

Notably, the above embodiment calculates the similarity of the red light AC component $AC_{red}$ and the infrared light AC component $AC_{IR}$ and the plurality of correlation coefficients of the red light AC component $AC_{red}$, to perform automatic signal quality detection and generate the reliability index RI of the physiological index accordingly, so as to assist the user to adjust the wearing position accordingly, thereby maintaining waveform with obvious periodicity and thus have high accuracy. Those skilled with in the art may make modifications or alterations accordingly, which are not limited to this. For example, the above embodiment is mainly described with the blood oxygen concentration SPO2, but in other embodiments, the reliability index RI may also indicate other physiological indexes such as heart rate, etc. The above embodiment utilizes two test signals and the template signal to calculate the correlation coefficients to generate the reliability index RI, but in other embodiments, it can also utilize other number of test signals and the reliability index RI may also indicate one of other numbers of signals qualities. Furthermore, the above embodiment utilizes the sample signal and the template signal of 2 seconds and the test signals of 1 second for calculation, in other embodiments, other sample periods may also be applied. When the sample period is extended, matching of sampled signals is more stringent, which requires the user to wear more well, and thus have more accurate measured blood oxygen concentration. For example, the sensing signal SEN is typically transmitted via Bluetooth. Because of data length limitation of Bluetooth, each transmission is a sampled signal of 2 seconds, and an extended sample period is 2n seconds. Signal lengths with the difference sample periods are as the following table:

| Sample signal | Template signal | Red light autocorrelation test signals | Red light and infrared light sample signal |
|---|---|---|---|
| 2 seconds | 2 seconds | 2 signals of 1 second | 2 seconds |
| 4 seconds | 4 seconds | 2 signals of 2 seconds | 4 seconds |
| 6 seconds | 6 seconds | 2 signals of 3 seconds | 6 seconds |
| 2 n seconds | 2 n seconds | 2 signals of n seconds | 2 n seconds |

In this case, for different user scenarios, different designs may be made to meet practical requirements. For example, for home measurement and tracking, although the accuracy of the present invention is slightly inferior to that of medical-grade equipment, it may track long-term and dynamically, which is the advantage of smart wearable devices. In addition, home use does not require instant measurement, and may apply longer sample signals listed in the above table to improve the accuracy of the calculation. The common symptoms of patients with COVID-19 are reduced blood oxygen levels, and the patients may not even detect that their own blood oxygen is low. The disadvantage of medical equipment is that they may only measure once. Such patients with chronic hypoxia may be performed with blood oxygen detection around the clock through the present invention, to observe the trend rather than absolute values, wherein real-time long-term measurement becomes extremely important. On the other hand, for a particular person engaged in sports such as mountain climbing, free diving, the need is convenience and real time measurement. Through monitoring of blood oxygen saturation concentration and real-time assessment of the physical condition, the current exercise intensity is adjusted. The group requires real-time feedback to track the trend of blood oxygen concentration, which is suitable for shorter sample period as listed in the above table for real time measurement.

On the other hand, in the above embodiment, after calculating the plurality of correlation coefficients $SQI_{xcorr}$ according to the red light test signals $T1_{Red}$, $T2_{Red}$ of the current red light sample signal $SAM_{Red}$ of 2 seconds, the reliability index RI of the oxygen concentration SPO2 is generated and directly outputted. However, in other embodiments, since the signal quality score indicated by the reliability index RI is sensitive and in real time, noise caused by slightly shaking may make the original signal quality falls from high to low, frequent changes of the index will make user hard to follow.

In addition, stable periodic waveform needs the previous sample signal as the template signal $TEM_{Red}$ for reference, and reference for the error template signal $TEM_{Red}$ should not be reflected to the user interface. Therefore, in addition to a current reliability index, a plurality of previous reliability indexes generated from previous calculations may be referred to decide the reliability index RI.

Figure 7:
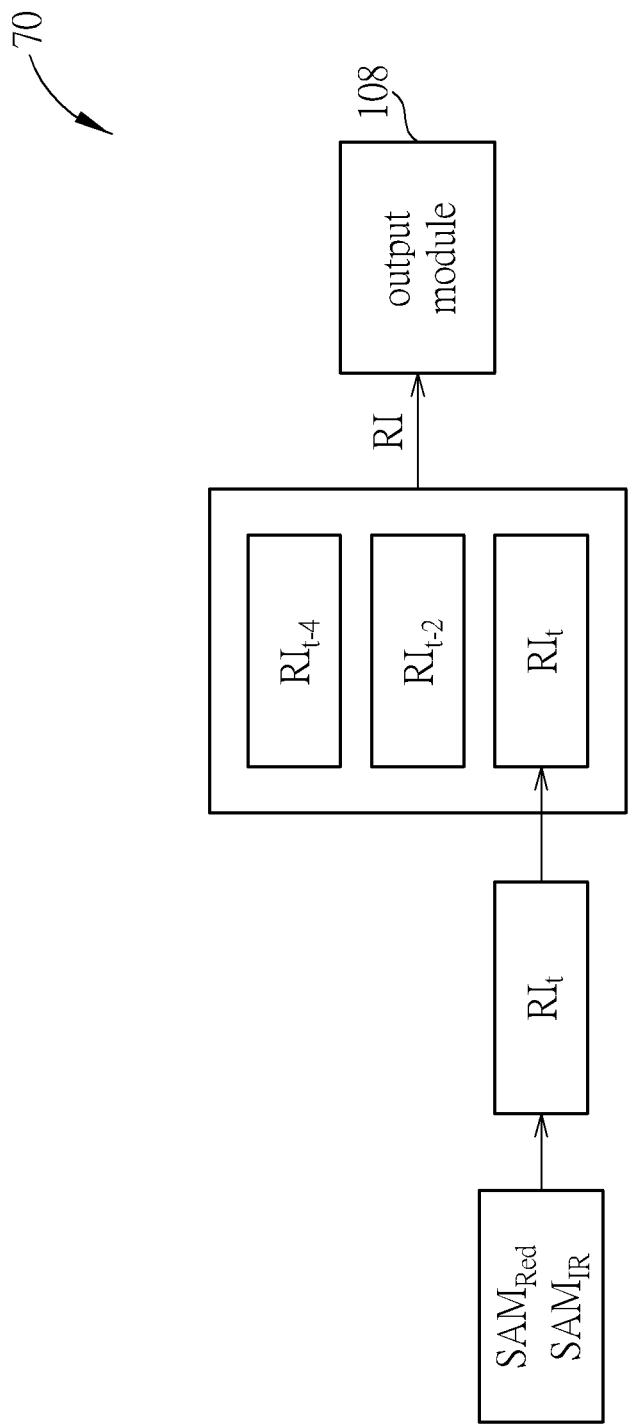
FIG. 7 is a schematic diagram of a reliability index determination process according to an embodiment of the present invention.

For example, an error sample signal in the current sample period may cause a current reliability index to indicate a low signal quality, and may cause the next reliability index to indicate a low signal quality when utilized as the template signal in the next sample period, so that two signal qualities indicated by two reliability indexes of the two previous sample signals are referred, to perform statistics on 3 signal qualities and adopt the highest as the current signal quality. In detail, please refer to FIG. 7, which is a schematic diagram of a reliability index determination process 70 according to an embodiment of the present invention. The signal quality detection module 106 generates a current reliability index $RI_t$ of an oxygen concentration SPO2 of according to the red light sample signal $SAM_{Red}$ and the infrared light sample signal $SAM_{IR}$ taken within the current sample period, and then generates the reliability index RI according to the current reliability index $RI_t$ and two previous reliability indexes $RI_{t-2}$, $RI_{t-4}$ generated in two previous sample periods, e.g. utilizing one of the current reliability index $RI_t$ and the previous reliability indexes $RI_{t-2}$, $RI_{t-4}$ indicating a highest one of the plurality of signal qualities as the reliability index RI. Generation of the current reliability index $RI_t$ and the previous reliability indexes $RI_{t-2}$, $RI_{t-4}$ may be derived by referring to the related contents of the above-mentioned similarity determination process 20 and the red light correlation determination process 30, and is not narrated here for brevity.

In this case, the reliability index determination process 70 may optimize the user experience, and avoid directly reacting to noise of small vibrations and frequently switching displayed signal qualities. The reliability index determination process 70 performs post-processed optimization, such that measurement of the signal quality indicated by the reliability index RI is less stringent (for example, indicate low signal quality when the current signal is good, because the referred template signal is interfered by noise). The reliability index determination process 70 may also refer to multiple time periods for statistics, to reduce errors and improve the reliability of signal quality determination. As a result, with respect to stringent wave examination, the present invention adopts a looser mechanism in accordance with the user's practical wear adjustment.

It is worth noting that in the above embodiment utilizes one of the current reliability index $RI_t$ and the previous reliability indexes $RI_{t-2}$, $RI_{t-4}$ indicating a highest one of the plurality of signal qualities as the reliability index RI. However, in other embodiments, the number of previous reliability indexes is not limited to two, and the current reliability index and a plurality of previous reliability indexes may be set with different weights, to emphasize the latest detection result while preventing short-term small vibration from causing the displayed signal quality to frequently switch. For example, weights of the current reliability index and three previous reliability indexes are set 0.4, 0.2, 0.2, 0.2, respectively. Therefore, when a short-term small vibrations only affects one sample period, the reliability index RI does not indicate a low signal quality, and when switching from a fit wearing position into an unfit wearing position, it may be within two sample periods, so that the reliability index RI may indicate a low signal quality accordingly, to allow the user to adjust to the wear position to reflect the recent detection results.

Figure 8:
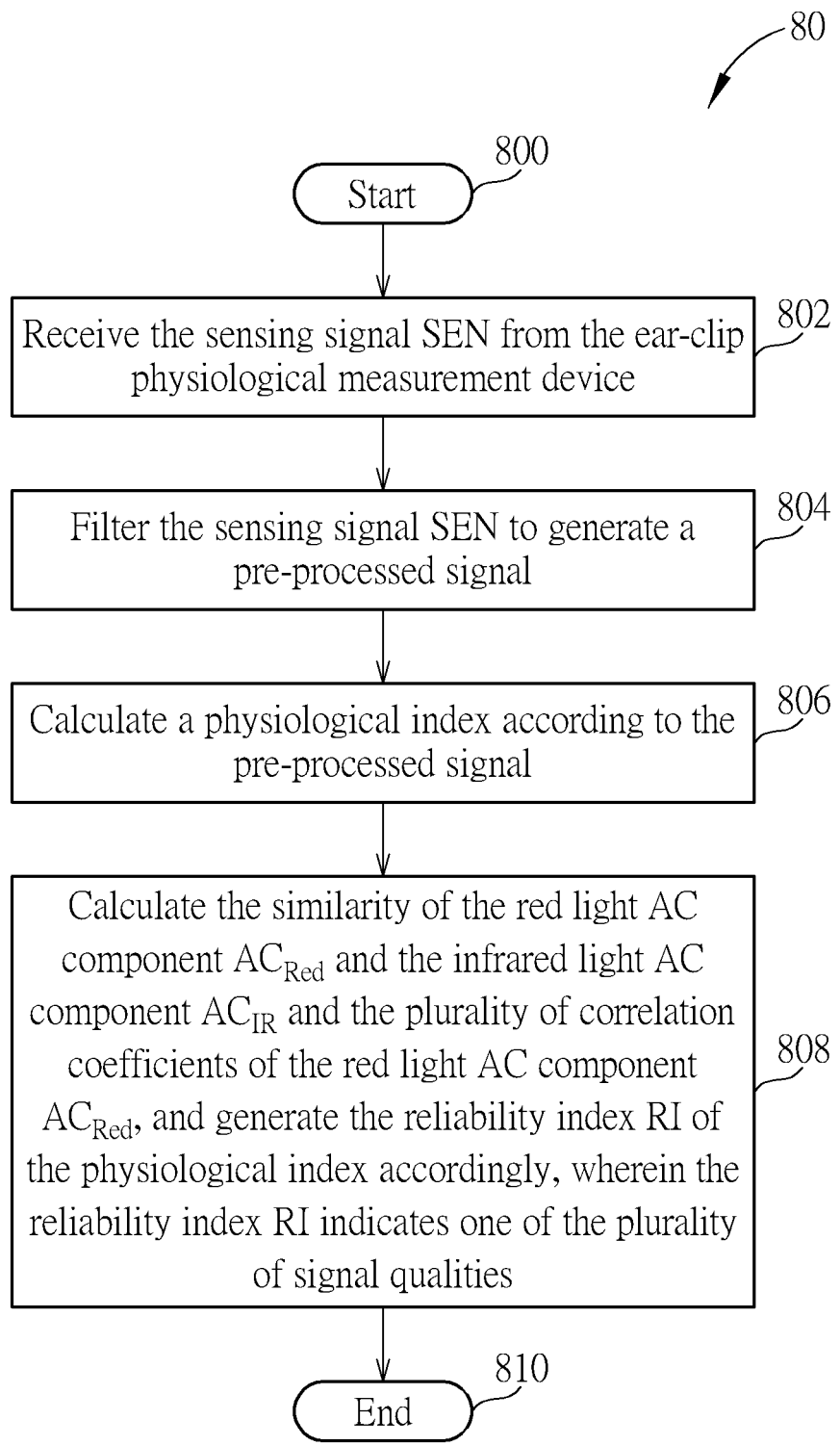
FIG. 8 is a schematic diagram of a signal quality detection process according to an embodiment of the present invention.

Thus, the signal quality detection operation of the signal detection device 10 may be summarized into a signal quality detection process 80 as shown in FIG. 8, and the signal quality detection process 80 includes following steps:

Step 800: Start.

Step 802: Receive the sensing signal SEN from the ear-clip physiological measurement device.

Step 804: Filter the sensing signal SEN to generate a pre-processed signal.

Step 806: Calculate a physiological index according to the pre-processed signal.

Step 808: Calculate the similarity of the red light AC component $AC_{red}$ and the infrared light AC component $AC_{IR}$ and the plurality of correlation coefficients of the red light AC component $AC_{red}$, and generate the reliability index RI of the physiological index accordingly, wherein the reliability index RI indicates one of the plurality of signal qualities.

Step 810: End.

Detailed operations of the signal quality detection process 80 may be referred to related contents of the signal detection device 10, and are omitted herein for brevity.

In addition, the signal detection device 10 may include a processor and a storage unit. The processor may be a microprocessor or an application-specific integrated circuit (ASIC). The storage unit may be any of a data storage device for storing a program code, and the processor reads and executes the program code to perform operations of the blood oxygen concentration calculation module 104 and the signal quality detection module 106, thereby completing the steps of the signal quality detection process 80. The storage unit may be subscriber identity module (SIM), read-only memory (ROM), random-access memory (RAM), CD-ROM read-only memory (CD-ROM), magnetic tapes, floppy disks, optical data storage devices, etc., but is not limited to these.

In summary, the present invention calculates the similarity of the red light AC component $AC_{red}$ and the infrared light AC component $AC_{IR}$ and the plurality of correlation coefficients of the red light AC component $AC_{red}$, to perform automatic signal quality detection and generate the reliability index RI of the physiological index accordingly, so as to assist the user to adjust the wearing position accordingly, thereby maintaining waveform with obvious periodicity and thus have high accuracy.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A signal quality detection method, for an ear-clip physiological measurement device, comprising:
receiving a sensing signal from the ear-clip physiological measurement device;
filtering the sensing signal to generate a pre-processed signal;
calculating a physiological index according to the pre-processed signal; and
calculating a similarity of a red light alternating current (AC) component and an infrared light AC component of the pre-processed signal and a plurality of correlation coefficients of the red light AC component, and generating a reliability index of the physiological index accordingly;
wherein the reliability index indicates one of a plurality of signal qualities;
wherein the step of calculating the similarity of the red light AC component and the infrared light AC component of the pre-processed signal and the plurality of correlation coefficients of the red light AC component, and generating the reliability index of the physiological index accordingly comprises:
utilizing the red light AC component retrieved within a previous sample period as a template signal;
dividing a red light sample signal retrieved within a current sample period into a plurality of red light test signals; and
calculating the plurality of correlation coefficients of the plurality of red light test signals and the template signal.

2. The signal quality detection method of claim 1, wherein the step of filtering the sensing signal to generate the pre-processed signal comprises:
performing bandpass filtering on the sensing signal to generate the red light AC component and the infrared light AC component of the pre-processed signal.

3. The signal quality detection method of claim 1, wherein the step of calculating the similarity of the red light AC component and the infrared light AC component of the pre-processed signal and the plurality of correlation coefficients of the red light AC component, and generating the reliability index of the physiological index accordingly comprises:
retrieving the red light AC component and the infrared light AC component within a sample period as a red light sample signal and an infrared light sample signal;
calculating the similarity of the red light sample signal and the infrared light sample signal; and
generating the reliability index indicating a low signal quality of the plurality of signal qualities when the similarity is less than a similarity threshold.

4. The signal quality detection method of claim 3 further comprising:
calculating the plurality of correlation coefficients of the red light AC component when the similarity is greater than the similarity threshold.

5. The signal quality detection method of claim 1, wherein the step of calculating the similarity of the red light AC component and the infrared light AC component of the pre-processed signal and the plurality of correlation coefficients of the red light AC component, and generating the reliability index of the physiological index accordingly further comprises:
generating the reliability index indicating the one of the plurality of signal qualities according to the plurality of correlation coefficients and a plurality of correlation thresholds.

6. The signal quality detection method of claim 5, wherein the step of generating the reliability index indicate the one of the plurality of signal qualities according to the plurality of correlation coefficients and the plurality of correlation thresholds comprises:
generating the reliability index indicating a low signal quality of the plurality of signal qualities if one of the plurality of correlation coefficients is less than a first correlation threshold;
generating the reliability index indicating a medium signal quality of the plurality of signal qualities if the plurality of correlation coefficients are between the first correlation threshold and a second correlation threshold, and generating the reliability index indicating a high signal quality of the plurality of signal qualities if the plurality of correlation coefficients are higher than the second correlation threshold.

7. The signal quality detection method of claim 5, wherein the step of calculating the similarity of the red light AC component and the infrared light AC component of the pre-processed signal and the plurality of correlation coefficients of the red light AC component, and generating the reliability index of the physiological index accordingly comprises:

generating the reliability index according to a current reliability index generated in the current sample period and a plurality of previous reliability indexes generated in a plurality of previous sample periods.

8. The signal quality detection method of claim 7, wherein the step of generating the reliability index according to the current reliability index generated in the current sample period and the plurality of previous reliability indexes generated in the plurality of previous sample periods comprises:

utilizing one of the current reliability index and the plurality of previous reliability indexes indicating a highest one of the plurality of signal qualities as the reliability index.

9. The signal quality detection method of claim 7, wherein the step of generating the reliability index according to the current reliability index generated in the current sample period and the plurality of previous reliability indexes generated in the plurality of previous sample periods comprises:

generating the reliability index according to a plurality of weights corresponding to the current reliability index and the plurality of previous reliability indexes, the current reliability index and the plurality of previous reliability indexes.

10. A signal detection device, for an ear-clip physiological measurement device, comprising:

an input module, for receiving a sensing signal from the ear-clip physiological measurement device;

a pre-processed module, for filtering the sensing signal to generate a pre-processed signal;

a processor, for executing a program code; and a storage unit, coupled to the processor, for storing the program code, wherein the program code is utilized for instructing the processor to perform following steps:

calculating a physiological index according to the pre-processed signal; and calculating a similarity of a red light alternating current (AC) component and an infrared light AC component of the pre-processed signal and a plurality of correlation coefficients of the red light AC component, and generating a reliability index of the physiological index accordingly;

wherein the reliability index indicates one of a plurality of signal qualities;

wherein the step of calculating the similarity of the red light AC component and the infrared light AC component of the pre-processed signal and the plurality of correlation coefficients of the red light AC component, and generating the reliability index of the physiological index accordingly comprises:

utilizing the red light AC component retrieved within a previous sample period as a template signal;

dividing a red light sample signal retrieved within a current sample period into a plurality of red light test signals; and calculating the plurality of correlation coefficients of the plurality of red light test signals and the template signal.

11. The signal detection device of claim 10, wherein the pre-processed module further comprises a bandpass filter, for performing bandpass filtering on the sensing signal to generate the red light AC component and the infrared light AC component of the pre-processed signal.

12. The signal detection device of claim 10, wherein the step of calculating the similarity of the red light AC component and the infrared light AC component of the pre-processed signal and the plurality of correlation coefficients of the red light AC component, and generating the reliability index of the physiological index accordingly comprises:

retrieving the red light AC component and the infrared light AC component within a sample period as a red light sample signal and an infrared light sample signal;

calculating the similarity of the red light sample signal and the infrared light sample signal; and generating the reliability index indicating a low signal quality of the plurality of signal qualities when the similarity is less than a similarity threshold.

13. The signal detection device of claim 12, wherein the program code further instructs the processor to perform following steps:

calculating the plurality of correlation coefficients of the red light AC component when the similarity is greater than the similarity threshold.

14. The signal detection device of claim 10, wherein the step of calculating the similarity of the red light AC component and the infrared light AC component of the pre-processed signal and the plurality of correlation coefficients of the red light AC component, and generating the reliability index of the physiological index accordingly further comprises:

generating the reliability index indicating the one of the plurality of signal qualities according to the plurality of correlation coefficients and a plurality of correlation thresholds.

15. The signal detection device of claim 14, wherein the step of generating the reliability index indicate the one of the plurality of signal qualities according to the plurality of correlation coefficients and the plurality of correlation thresholds comprises:

generating the reliability index indicating a low signal quality of the plurality of signal qualities if one of the plurality of correlation coefficients is less than a first correlation threshold, generating the reliability index indicating a medium signal quality of the plurality of signal qualities if the plurality of correlation coefficients are between the first correlation threshold and a second correlation threshold, and generating the reliability index indicating a high signal quality of the plurality of signal qualities if the plurality of correlation coefficients are higher than the second correlation threshold.

16. The signal detection device of claim 14, the step of calculating the similarity of the red light AC component and the infrared light AC component of the pre-processed signal and the plurality of correlation coefficients of the red light AC component, and generating the reliability index of the physiological index accordingly comprises:

generating the reliability index according to a current reliability index generated in the current sample period and a plurality of previous reliability indexes generated in a plurality of previous sample periods.

17. The signal detection device of claim 16, wherein the step of generating the reliability index according to the current reliability index generated in the current sample period and the plurality of previous reliability indexes generated in the plurality of previous sample periods comprises:
utilizing one of the current reliability index and the plurality of previous reliability indexes indicating a highest one of the plurality of signal qualities as the reliability index.

18. The signal detection device of claim 16, wherein the step of generating the reliability index according to the current reliability index generated in the current sample period and the plurality of previous reliability indexes generated in the plurality of previous sample periods comprises:
generating the reliability index according to a plurality of weights corresponding to the current reliability index and the plurality of previous reliability indexes, the current reliability index and the plurality of previous reliability indexes.

\* \* \* \* \*